(12) United States Patent
Robvieux et al.

(10) Patent No.: US 12,423,711 B2
(45) Date of Patent: Sep. 23, 2025

(54) SUSTAINABLE FRAGRANCE OR FLAVOUR COMPOSITION METHODS AND ASSOCIATED DEVICE

(71) Applicant: Firmenich SA, Satigny (CH)

(72) Inventors: Fabrice Robvieux, Satigny (CH); Maud Reiter, Satigny (CH); Hazal Ustundag George, Satigny (CH); Juliette Sicot-Crevet, Satigny (CH); Gilles Oddon, Satigny (CH); Sven Jeanrenaud, Satigny (CH); Johanna Levy, Satigny (CH)

( * ) Notice: Subject to any disclaimer, the term of this patent is extended or adjusted under 35 U.S.C. 154(b) by 0 days.

(21) Appl. No.: 17/942,608

(22) Filed: Sep. 12, 2022

(65) Prior Publication Data

US 2024/0202741 A1    Jun. 20, 2024

(51) Int. Cl.
*G06Q 30/018* (2023.01)
*G06F 16/22* (2019.01)
(Continued)

(52) U.S. Cl.
CPC ........... *G06Q 30/018* (2013.01); *G06F 16/22* (2019.01); *G16C 20/00* (2019.02); *G16C 20/90* (2019.02); *G16C 60/00* (2019.02)

(58) Field of Classification Search
CPC ...... G06Q 30/018; G06F 16/22; G16C 20/00; G16C 60/00; G16C 20/90
See application file for complete search history.

(56) References Cited

U.S. PATENT DOCUMENTS

| | | | |
|---|---|---|---|
| 2018/0060450 A1* | 3/2018 | McNamara | G06F 30/00 |
| 2020/0365053 A1* | 11/2020 | Pichara | G01N 33/12 |
| 2021/0037863 A1* | 2/2021 | Pichara | G06F 18/2431 |

FOREIGN PATENT DOCUMENTS

FR    3103363 A1 *    5/2021 ......... G06Q 30/0621

OTHER PUBLICATIONS

Symrise (Ingredient Finder, Symrise, Aug. 2, 2021, WayBack Machine, https://web.archive.org/web/20210802143734/https://www.symrise.com/scent-and-care/aroma-molecules/ingredient-finder/) (Year: 2021).*

(Continued)

*Primary Examiner* — Lisa M Caputo
*Assistant Examiner* — Christian T Bryant
(74) *Attorney, Agent, or Firm* — Patshegen IP; Moshe Pinchas

(57) ABSTRACT

The computer-implemented fragrance or flavour composition method (300), comprises:
  a step (305) of defining, upon a computer interface, a value representative of a sustainability impact digital index or of an aggregate sustainability impact digital indicator validity threshold for at least one fragrance or flavour ingredient in the fragrance or flavour composition, said fragrance or flavour ingredient being associated to a fragrance or flavour ingredient digital identifier, or to a fragrance or flavour composition digital identifier,
  a step (310) of selecting, upon a computer interface, at least one fragrance or flavour ingredient digital identifier,
  a step (315) of retrieval, by a computing device, from a fragrance or flavour ingredient physical parameter database of a sustainability impact digital index or of an aggregate sustainability impact digital indicator as a function of at least one said fragrance or flavour ingredient digital identifier,
  a step (320) of comparing, by a computing device, as a function of at least one selected fragrance or flavour ingredient digital identifier, a sustainability impact digital index or of an aggregate sustainability impact digital indicator retrieved to the validity threshold defined and (Continued)

a step (325) of providing, upon a computer interface, an indicator representative of the result of the step of comparing.

13 Claims, 6 Drawing Sheets

(51) Int. Cl.
    *G16C 20/00*     (2019.01)
    *G16C 20/90*     (2019.01)
    *G16C 60/00*     (2019.01)

(56)        References Cited

OTHER PUBLICATIONS

Salvito et al. (A framework for prioritizing fragrance materials for aquatic risk assessment. Environ Toxicol Chem. Jun. 2002;21(6): 1301-8. PMID: 12069318.) (Year: 2002).*

Bickers et al. (The safety assessment of fragrance materials, Regulatory Toxicology and Pharmacology, vol. 37, Issue 2, 2003, pp. 218-273, ISSN 0273-2300, https://doi.org/10.1016/S0273-2300(03)00003-5.) (Year: 2003).*

* cited by examiner

SUSTAINABLE FRAGRANCE OR FLAVOUR COMPOSITION METHODS AND ASSOCIATED DEVICE

RELATED APPLICATIONS

The present application claims priority to European Patent Application No. 21195913.5, filed Sep. 10, 2021. The entire contents of this application is explicitly incorporated herein by this reference.

TECHNICAL FIELD OF THE INVENTION

The present invention relates to a computer-implemented fragrance or flavour ingredient or composition of said ingredients physical parameter database construction method, computer-implemented sustainable fragrance or flavour composition methods, a fragrance or flavour ingredient or composition of said ingredients physical parameter database construction device and a sustainable fragrance or flavour composition device. It applies, in particular, to the fields of fragrance design, ingredient performance evaluation, perfumery, fine fragrance perfumery and flavour design.

BACKGROUND OF THE INVENTION

Fragrance design can be defined as the selection of at least one fragrant ingredient to form a composition intended to provide a hedonic impression. Fragrance design is most notably known in the field of perfumery and is performed by perfumers.

The evaluation of a fragrance is typically based on performance metrics and fragrance hedonics. However, sustainability imperatives require the additional considerations of sustainability externalities associated with the fragrant ingredients used. While methodologies to evaluate the sustainability burden of generating particular ingredients may be known, none are comprehensive enough in their approach nor are such methodologies used in the context of fragrance design.

As such, the environmental footprint of fragrances remains largely unknown and thus cannot be acted upon by perfumers.

SUMMARY OF THE INVENTION

The present invention is intended to remedy all or part of these disadvantages.

To this effect, according to a first aspect, the present invention aims at a computer-implemented fragrance or flavour ingredient or composition of said ingredients physical parameter database construction method, comprising:
  a step of collection, upon a computer interface, of at least one value representative of a measurable sustainability physical parameter, said physical parameter being representative of an intrinsic sustainability physical parameter of the fragrance or flavour ingredient or of a measurable sustainability physical parameter representative of a manufacturing process associated to the fragrance or flavour ingredient, said fragrance or flavour ingredient being associated to a fragrance or flavour ingredient digital identifier, at least one said physical parameter being representative of:
    the carbon renewability of the fragrance or flavour ingredient,
    the biodegradability of the fragrance or flavour ingredient,
    a quantity or proportion of upcycled ingredients used to obtain the fragrance or flavour ingredient,
    a quantity or proportion of biotechnologically processed ingredients used to obtain the fragrance or flavour ingredient,
    a quantity or proportion of renewable raw materials used to obtain the fragrance or flavour ingredient,
    the carbon dioxide equivalent footprint of the fragrance or flavour ingredient or
    a quantity or proportion of organic raw materials used to obtain the fragrance or flavour ingredient,
  a step of computation, by a computing device, of a sustainability impact digital index for the fragrance or flavour ingredient digital identifier and
  a step of storing, in a database, the computed sustainability impact digital index for the fragrance or flavour ingredient digital identifier.

Such provisions allow for the constitution of a database of sustainability physical parameters of known fragrance or flavour ingredients. Such a database may be used by perfumers during a step of fragrance design. The knowledge gathered within the database allows for more sustainable and environmentally friendly compositions to be assembled. The sustainability impact digital index can be used in further digital applications thus allowing for smarter decision-making on behalf of users. Depending on the use case considered, such metrics can be obtained in more or less complex manners.

In particular embodiments, at least one sustainability impact digital index is representative of:
  a ratio of a number of carbons of the fragrance or flavour ingredient over a number of carbons in the reactants and reagents used to obtain the fragrance or flavour ingredient,
  a number of catalytic steps required to obtain the fragrance or flavour ingredient,
  a hazardousness of the reactants, solvents and reagents used to obtain the fragrance or flavour ingredient,
  a quantity or proportion of essential oils used to obtain the fragrance or flavour ingredient,
  a surface area of land used to obtain the fragrance or flavour ingredient,
  a quantity of waste generated to obtain the fragrance or flavour ingredient,
  a quantity or proportion of water used to obtain the fragrance or flavour ingredient,
  a quantity or proportion of palm oil or palm oil derivatives used to obtain the fragrance or flavour ingredient and/or
  the environmental toxicity of the fragrance or flavour ingredient.

ingredientingredientingredientingredientingredientingredientingredie ntingredientingredientingredientingredientSuch embodiments allow for the constitution of an extensive database relative to a variety of sustainability impacts of fragrance or flavour ingredients. The accumulation of such indexes allows for a finer, more accurate fragrance design process by users. Such indexes may further be used to develop and/or improve current chemical synthesis of fragrance or flavour ingredients.

In particular embodiments, at least one sustainability impact digital index is representative of a number of catalytic steps required to obtain the fragrance or flavour ingredient.

In particular embodiments, at least one sustainability impact digital index is representative of a hazardousness of the reactants, solvents and reagents used to obtain the fragrance or flavour ingredient.

In particular embodiments, at least one sustainability impact digital index is representative of a ratio of a number of carbons of the fragrance or flavour ingredient over a number of carbons in the reactants and reagents used to obtain the fragrance or flavour ingredient.

In particular embodiments, the method object of the present invention further comprises a step of determination, by a computing device, of an aggregate sustainability impact digital indicator as a function of at least two different sustainability impact digital indexes for the fragrance or flavour ingredient digital identifier.

Such embodiments allow for the constitution of intermediate aggregates, each aggregate being representative of a subset of lower-level indexes. Such embodiments further allow the presentation of a limited amount of information to a user, allowing for faster decision-making.

According to a second aspect, the present invention aims at a computer-implemented fragrance or flavour composition method, comprising:
- a step of defining, upon a computer interface, a value representative of a sustainability impact digital index or of an aggregate sustainability impact digital indicator validity threshold for at least one fragrance or flavour ingredient in the fragrance or flavour composition, said fragrance or flavour ingredient being associated to a fragrance or flavour ingredient digital identifier, or to the fragrance or flavour composition, at least one said physical parameter being representative of:
  - the carbon renewability of the fragrance or flavour ingredient,
  - the biodegradability of the fragrance or flavour ingredient,
  - a quantity or proportion of upcycled ingredients used to obtain the fragrance or flavour ingredient,
  - a quantity or proportion of biotechnologically processed ingredients used to obtain the fragrance or flavour ingredient,
  - a quantity or proportion of renewable raw materials used to obtain the fragrance or flavour ingredient,
  - the carbon dioxide equivalent footprint of the fragrance or flavour ingredient or
  - a quantity or proportion of organic raw materials used to obtain the fragrance or flavour ingredient,
- a step of selecting, upon a computer interface, at least one fragrance or flavour ingredient digital identifier,
- a step of retrieval, by a computing device, from a fragrance or flavour ingredient physical parameter database of a sustainability impact digital index or of an aggregate sustainability impact digital indicator as a function of at least one said fragrance or flavour ingredient digital identifier
- a step of comparing, by a computing device, as a function of at least one selected fragrance or flavour ingredient digital identifier, a sustainability impact digital index or of an aggregate sustainability impact digital indicator retrieved to the validity threshold defined and
- a step of providing, upon a computer interface, an indicator representative of the result of the step of comparing.

The advantages of such a method are similar to the advantages of the method object of the first aspect of the present invention. In particular, such provisions allow for dynamic fragrance or flavour composition as a function of the threshold set. using such a threshold allows for fragrance or flavour composition to fit into determined environmental and sustainability constraints.

In particular embodiments, the method object of the present invention further comprises, downstream of the step of retrieval, a step of computing, by a computing device, an aggregate sustainability impact digital indicator as a function of at least one sustainability impact digital index retrieved, said aggregate sustainability impact digital indicator being used in the step of comparing.

Such embodiments allow for the use of intermediate indicators representative of a subset of sustainability impact digital indexes. Such intermediate calculations allow for a more nuanced fragrance or flavour composition process wherein a specific threshold targets a composite group of indexes rather than only applying to one.

In particular embodiments, the method object of the present invention further comprises a step of defining, upon a computer interface, a value representative of a quantity of fragrance or flavour ingredient, said value being used in the step of computing.

Such embodiments allow for a more accurate representation of the fragrance or flavour composition to be assembled. In particular, the impact of an unfavourable environmental footprint of a fragrance or flavour ingredient may be counterbalanced by a relatively small quantity of such a fragrance or flavour ingredient within a composition.

In particular embodiments, the method object of the present invention further comprises:
- a step of electing, by a computing device, at least one candidate fragrance or flavour ingredient digital identifier as a replacement for at least one selected fragrance or flavour ingredient digital identifier as a function of said at least one selected fragrance or flavour ingredient digital identifier and
- a step of providing, upon a computer interface, at least one candidate fragrance or flavour ingredient digital identifier elected.

Such embodiments allow for dynamic fragrance or flavour composition in which a candidate fragrance or flavour ingredient may be selected instead of an initially selected fragrance or flavour ingredient, should said candidate fragrance or flavour ingredient provide better environmental performance.

In particular embodiments, the method object of the present invention further comprises:
- a step of calculating, by a computing device, a value representative of a quantity or proportion of at least one selected fragrance or flavour ingredient digital identifier as a function of the validity threshold defined and
- a step of providing, upon a computer interface, the quantity calculated.

Such embodiments allow for dynamic fragrance or flavour composition in which the quantity of a particular fragrance or flavour ingredient may be dynamically adjusted to limit the impact of said fragrance or flavour ingredient on the overall environmental performance of the composition.

In particular embodiments, the method object of the present invention further comprises a step of assembling the fragrance or flavour composition as a function of at least one selected fragrance or flavour ingredient digital identifier.

Such embodiments allow for the assembly of the designed fragrance or flavour composition.

In particular embodiments, the method object of the present invention comprises a computer-implemented fragrance or flavour ingredient or composition of said ingredients physical parameter database construction step, comprising:
- a step of collection, upon a computer interface, of at least one value representative of a measurable sustainability physical parameter, said physical parameter being representative of an intrinsic sustainability physical parameter of the fragrance or flavour ingredient or of a measurable sustainability physical parameter representative of a manufacturing process associated to the fragrance or flavour ingredient, said fragrance or flavour ingredient being associated to a fragrance or flavour ingredient digital identifier, at least one said physical parameter being representative of:
- the carbon renewability of the fragrance or flavour ingredient,
- the biodegradability of the fragrance or flavour ingredient,
- a quantity or proportion of upcycled ingredients used to obtain the fragrance or flavour ingredient,
- a quantity or proportion of biotechnologically processed ingredients used to obtain the fragrance or flavour ingredient,
- a quantity or proportion of renewable raw materials used to obtain the fragrance or flavour ingredient,
- the carbon dioxide equivalent footprint of the fragrance or flavour ingredient or
- a quantity or proportion of organic raw materials used to obtain the fragrance or flavour ingredient,
- a step of computation, by a computing device, of a sustainability impact digital index for the fragrance or flavour ingredient digital identifier and
- a step of storing, in a database, the computed sustainability impact digital index for the fragrance or flavour ingredient digital identifier.

In particular embodiments, at least one sustainability impact digital index is representative of:
- a ratio of a number of carbons of the fragrance or flavour ingredient over a number of carbons in the reactants and reagents used to obtain the fragrance or flavour ingredient,
- a number of catalytic steps required to obtain the fragrance or flavour ingredient,
- a hazardousness of the reactants, solvents and reagents used to obtain the fragrance or flavour ingredient,
- a quantity or proportion of essential oils used to obtain the fragrance or flavour ingredient,
- a surface area of land used to obtain the fragrance or flavour ingredient,
- a quantity of waste generated to obtain the fragrance or flavour ingredient,
- a quantity or proportion of water used to obtain the fragrance or flavour ingredient,
- a quantity or proportion of palm oil or palm oil derivatives used to obtain the fragrance or flavour ingredient and/or
- the environmental toxicity of the fragrance or flavour ingredient.

In particular embodiments, at least one sustainability impact digital index is representative of a number of catalytic steps required to obtain the fragrance or flavour ingredient.

In particular embodiments, at least one sustainability impact digital index is representative of a hazardousness of the reactants, solvents and reagents used to obtain the fragrance or flavour ingredient.

In particular embodiments, at least one sustainability impact digital index is representative of a ratio of a number of carbons of the fragrance or flavour ingredient over a number of carbons in the reactants and reagents used to obtain the fragrance or flavour ingredient.

In particular embodiments, the method object of the present invention further comprises a step of determination, by a computing device, of an aggregate sustainability impact digital indicator as a function of at least two different sustainability impact digital indexes for the fragrance or flavour ingredient digital identifier.

According to a third aspect, the present invention aims at a computer-implemented fragrance or flavour composition method, comprising:
- a step of selecting, upon a computer interface, at least one fragrance or flavour ingredient digital identifier,
- a step of retrieval, by a computing device, from a fragrance or flavour ingredient physical parameter database obtained of a sustainability impact digital index or of an aggregate sustainability impact digital indicator as a function of at least one said fragrance or flavour ingredient digital identifier, at least one said physical parameter being representative of:
  - the carbon renewability of the fragrance or flavour ingredient,
  - the biodegradability of the fragrance or flavour ingredient,
  - a quantity or proportion of upcycled ingredients used to obtain the fragrance or flavour ingredient,
  - a quantity or proportion of biotechnologically processed ingredients used to obtain the fragrance or flavour ingredient,
  - a quantity or proportion of renewable raw materials used to obtain the fragrance or flavour ingredient,
  - the carbon dioxide equivalent footprint of the fragrance or flavour ingredient or
  - a quantity or proportion of organic raw materials used to obtain the fragrance or flavour ingredient,
- a step of calculating, by a computing device, a value representative of a quantity or proportion of at least one selected fragrance or flavour ingredient digital identifier as a function of the validity threshold defined and
- a step of providing, upon a computer interface, the quantity calculated.

According to a fourth aspect, the present invention aims at a fragrance or flavour ingredient or composition of said ingredients physical parameter database construction device, comprising:
- a step of selecting, upon a computer interface, at least one fragrance or flavour ingredient digital identifier,
- a step of retrieval, by a computing device, from a fragrance or flavour ingredient physical parameter database of a sustainability impact digital index or of an aggregate sustainability impact digital indicator as a function of at least one said fragrance or flavour ingredient digital identifier, at least one said physical parameter being representative of:
  - the carbon renewability of the fragrance or flavour ingredient,
  - the biodegradability of the fragrance or flavour ingredient,
  - a quantity or proportion of upcycled ingredients used to obtain the fragrance or flavour ingredient,
  - a quantity or proportion of biotechnologically processed ingredients used to obtain the fragrance or flavour ingredient,
  - a quantity or proportion of renewable raw materials used to obtain the fragrance or flavour ingredient,
  - the carbon dioxide equivalent footprint of the fragrance or flavour ingredient or
  - a quantity or proportion of organic raw materials used to obtain the fragrance or flavour ingredient,
- a step of electing, by a computing device, at least one candidate fragrance or flavour ingredient digital identifier as a replacement for at least one selected fragrance or flavour ingredient digital identifier as a function of said at least one selected fragrance or flavour ingredient digital identifier and a step of providing, upon a computer interface, at least one candidate fragrance or flavour ingredient digital identifier elected.

According to a fifth aspect, the present invention aims at a computer-implemented fragrance or flavour composition method, comprising:

a step of selecting, upon a computer interface, at least two fragrance or flavour ingredient digital identifiers, a step of retrieval, by a computing device, from a fragrance or flavour ingredient physical parameter database obtained of a sustainability impact digital index or of an aggregate sustainability impact digital indicator as a function of at least two said fragrance or flavour ingredient digital identifier, at least one said physical parameter being representative of:
   the carbon renewability of the fragrance or flavour ingredient,
   the biodegradability of the fragrance or flavour ingredient,
   a quantity or proportion of upcycled ingredients used to obtain the fragrance or flavour ingredient,
   a quantity or proportion of biotechnologically processed ingredients used to obtain the fragrance or flavour ingredient,
   a quantity or proportion of renewable raw materials used to obtain the fragrance or flavour ingredient,
   the carbon dioxide equivalent footprint of the fragrance or flavour ingredient or
   a quantity or proportion of organic raw materials used to obtain the fragrance or flavour ingredient, a step of computing an aggregate sustainability impact digital indicator as a function of at least two sustainability impact digital index retrieved and a step of providing, upon a computer interface, the computed aggregate sustainability impact digital indicator.

According to a sixth aspect of the present invention, the present invention aims at a fragrance or flavour ingredient physical parameter database construction device, comprising:

a means of collection, upon a computer interface, of at least one value representative of a measurable sustainability physical parameter, said physical parameter being representative of an intrinsic sustainability physical parameter of the fragrance or flavour ingredient or of a measurable sustainability physical parameter representative of a manufacturing process associated to the fragrance or flavour ingredient, said fragrance or flavour ingredient being associated to a fragrance or flavour ingredient digital identifier, at least one said physical parameter being representative of:
   the carbon renewability of the fragrance or flavour ingredient,
   the biodegradability of the fragrance or flavour ingredient,
   a quantity or proportion of upcycled ingredients used to obtain the fragrance or flavour ingredient,
   a quantity or proportion of biotechnologically processed ingredients used to obtain the fragrance or flavour ingredient,
   a quantity or proportion of renewable raw materials used to obtain the fragrance or flavour ingredient,
   the carbon dioxide equivalent footprint of the fragrance or flavour ingredient or
   a quantity or proportion of organic raw materials used to obtain the fragrance or flavour ingredient, a means of computation, by a computing device, of a sustainability impact digital index for the fragrance or flavour ingredient digital identifier and a means of storing, in a database, the computed sustainability impact digital index for the fragrance or flavour ingredient digital identifier.

The advantages of such a method are similar to the advantages of the method object of the first aspect of the present invention.

According to a seventh aspect of the present invention, the present invention aims at a fragrance or flavour composition device, comprising:

a means of defining, upon a computer interface, a value representative of a sustainability impact digital index or of an aggregate sustainability impact digital indicator validity threshold for at least one fragrance or flavour ingredient in the fragrance or flavour composition, said fragrance or flavour ingredient being associated to a fragrance or flavour ingredient digital identifier, or to a fragrance or flavour composition digital identifier, a means of selecting, upon a computer interface, at least one fragrance or flavour ingredient digital identifier, a means of retrieval, by a computing device, from a fragrance or flavour ingredient physical parameter database of a sustainability impact digital index or of an aggregate sustainability impact digital indicator as a function of at least one said fragrance or flavour ingredient digital identifier, at least one said physical parameter being representative of:
   the carbon renewability of the fragrance or flavour ingredient,
   the biodegradability of the fragrance or flavour ingredient,
   a quantity or proportion of upcycled ingredients used to obtain the fragrance or flavour ingredient,
   a quantity or proportion of biotechnologically processed ingredients used to obtain the fragrance or flavour ingredient,
   a quantity or proportion of renewable raw materials used to obtain the fragrance or flavour ingredient,
   the carbon dioxide equivalent footprint of the fragrance or flavour ingredient or
   a quantity or proportion of organic raw materials used to obtain the fragrance or flavour ingredient, a means of comparing, by a computing device, as a function of at least one selected fragrance or flavour ingredient digital identifier, a sustainability impact digital index or of an aggregate sustainability impact digital indicator retrieved to the validity threshold defined and a means of providing, upon a computer interface, an indicator representative of the result of the step of comparing.

The advantages of such a method are similar to the advantages of the method object of the second aspect of the present invention.

BRIEF DESCRIPTION OF THE DRAWINGS

Other advantages, purposes and particular characteristics of the invention shall be apparent from the following non-exhaustive description of at least one particular method or device which is the subject of this invention, in relation to the drawings annexed hereto, in which.

DETAILED DESCRIPTION OF THE INVENTION

Figure 1:
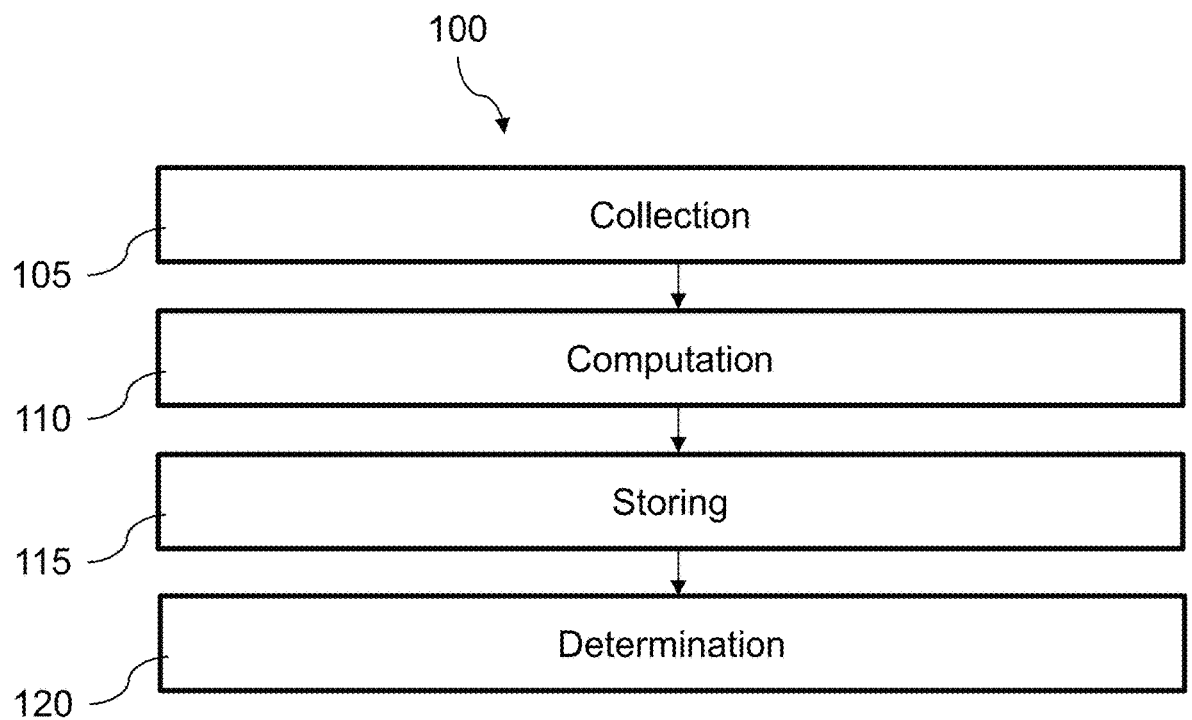
FIG. 1 represents, schematically and in the form of a flowchart, a particular succession of steps of the database construction method, which is the object of the present invention.

This description is not exhaustive, as each feature of one embodiment may be combined with any other feature of any other embodiment in an advantageous manner.

It should be noted that the figures are not to scale.

In the context of this invention, a "fragrance or flavour ingredient" designates a perfuming ingredient, a flavour ingredient, a perfumery carrier, a flavour carrier, a perfumery adjuvant, a flavour adjuvant, a perfumery modulator, flavour modulator. Preferably, such a fragrance or flavour ingredient is volatile.

By "perfuming ingredient" it is meant here a compound, which is used in a perfuming preparation or a composition to impart a hedonic effect. In other words, such an ingredient, to be considered as being a perfuming one, must be recognised by a person skilled in the art as being able to impart or modify in a positive or pleasant way the odour of a composition, and not just as having an odour.

The nature and type of the perfuming ingredients do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Said perfuming ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said perfuming ingredients may also be compounds known to release in a controlled manner various types of perfuming ingredients also known as properfume or profragrance.

By "perfumery carrier" it is meant here a material which is practically neutral from a perfumery point of view, i.e., that does not significantly alter the organoleptic properties of perfuming ingredients. Said carrier may be a liquid or a solid.

As liquid carrier one may cite, as non-limiting examples, an emulsifying system, i.e., a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate and dimethyl adipate 1,3-diacetyloxypropan-2-yl acetate or mixtures thereof, which are the most commonly used. For the compositions which comprise both a perfumery carrier and a perfumery base, other suitable perfumery carriers than those previously specified, can also be ethanol, water/ethanol mixtures, limonene or other terpenes.

Solid carrier is meant to designate a material to which the perfuming composition or some element of the perfuming composition can be chemically or physically bound. In general, such solid carriers are employed either to stabilise the composition, or to control the rate of evaporation of the compositions or of some ingredients. The use of solid carriers is of current use in the art and a person skilled in the art knows how to reach the desired effect. However, by way of non-limiting examples of solid carriers, one may cite absorbing gums or polymers or inorganic materials, such as porous polymers, cyclodextrins, wood-based materials, organic or inorganic gels, clays, gypsum talc or zeolites.

As other non-limiting examples of solid carriers, one may cite encapsulating materials. Examples of such materials may comprise wall-forming and plasticising materials, such as mono, di- or trisaccharides, natural or modified starches, hydrocolloids, cellulose derivatives, polyvinyl acetates, polyvinylalcohols, proteins or pectins. The encapsulation is a well-known process to a person skilled in the art, and may be performed, for instance, by using techniques such as spray-drying, agglomeration or yet extrusion; or consists of a coating encapsulation, including coacervation and complex coacervation techniques.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerisation, interfacial polymerisation, coacervation or altogether (all of said techniques have been described in the prior art).

Resins may be produced by the polycondensation of an aldehyde (e.g., formaldehyde, 2,2-dimethoxyethanal, glyoxal, glyoxylic acid or glycolaldehyde and mixtures thereof) with an amine such as urea, benzoguanamine as well as mixtures thereof.

Others resins one are the ones produced by the polycondensation of a polyol, like glycerol, and a polyisocyanate, like a trimer of hexamethylene diisocyanate, a trimer of isophorone diisocyanate or xylylene diisocyanate or a Biuret of hexamethylene diisocyanate.

Some of the seminal literature related to the encapsulation of perfumes by polycondensation of amino resins, namely melamine-based resins with aldehydes includes represented by articles such as those published by K. Dietrich et al. Acta Polymerica, 1989, vol. 40, pages 243, 325 and 683, as well as 1990, vol. 41, page 91.

By "perfumery adjuvant," it is meant here an ingredient capable of imparting additional added benefit such as a colour, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilising agents (e.g. preservatives, antioxidants, heat/light and or buffers or chelating agents, such as BHT), colouring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

By "perfumery modulator", it is understood here an agent having the capacity to affect the manner in which the odour, and in particular the evaporation rate and intensity, of the compositions incorporating said modulator can be perceived by an observer or user thereof, over time, as compared to the same perception in the absence of the modulator. Perfumery modulators are also known as fixative. In particular, the modulator allows prolonging the time during which their fragrance is perceived. Non-limiting examples of suitable modulators may include methyl glucoside polyol; ethyl glucoside polyol; propyl glucoside polyol; isocetyl alcohol; PPG-3 myristyl ether; and their mixtures; neopentyl glycol diisononanoate; cetearyl ethylhexanoate; panthenol ethyl ether, DL-panthenol, N-hexadecyl n-nonanoate, noctadecyl n-nonanoate, a profragrance, cyclodextrin, an encapsulation, and a combination thereof.

By "flavouring ingredient" it is meant here a compound, which is used in flavouring preparations or compositions to impart a hedonic effect. In other words, such an ingredient, to be considered as being a flavouring one, must be recognised by a person skilled in the art as being able to impart or modify in a positive or pleasant way the taste of a composition, and not just as having a taste. The nature and type of the flavouring ingredients present in the composition do not warrant a more detailed description here, the skilled person being able to select them on the basis of its general knowledge and according to intended use or application and the desired organoleptic effect. In general terms, these flavouring ingredients belong to chemical classes as varied as alcohols, aldehydes, ketones, esters, ethers, acetates, nitriles, terpenoids, nitrogenous, and said flavouring ingredients can be of natural or synthetic origin.

The term "organic" refers both to organic ingredients and to third-party certified sourced feedstock.

The term "flavour carrier" designates a material which is substantially neutral from a flavour point of view, as far as it does not significantly alter the organoleptic properties of flavouring ingredients. The carrier may be a liquid or a solid.

Suitable liquid carriers include, for instance, an emulsifying system, i.e., a solvent and a surfactant system, or a solvent commonly used in flavours. A detailed description of the nature and type of solvents commonly used in flavour cannot be exhaustive. Suitable solvents used in flavour include, for instance, propylene glycol, triacetine, caprylic/capric or coconut oil, glycerol.

Suitable solid carriers include, for instance, absorbing gums or polymers, or even encapsulating materials. Examples of such materials may comprise wall-forming and plasticising materials, such as mono, di- or polysaccharides, natural or modified starches, hydrocolloids, cellulose derivatives, polyvinyl acetates, polyvinylalcohols or xanthan gum, Encapsulation is a well-known process to a person skilled in the art, and may be performed, for instance, using techniques such as spray-drying, agglomeration, extrusion, coating, plating, coacervation and the like.

By "flavour adjuvant," it is meant here an ingredient capable of imparting additional added benefit such as a colour (e.g., caramel), chemical stability, and so on. A detailed description of the nature and type of adjuvant commonly used in flavouring compositions cannot be exhaustive. Nevertheless, such adjuvants are well known to a person skilled in the art who will be able to select them on the basis of its general knowledge and according to intended use or application. One may cite as specific non-limiting examples the following: viscosity agents (e.g., emulsifier, thickeners, gelling and/or rheology modifiers, e.g. pectin or agar gum), stabilising agents (e.g. antioxidant, heat/light and or buffers agents e.g. citric acid), colouring agents (e.g. natural or synthetic or natural extract imparting colour), preservatives (e.g. antibacterial or antimicrobial or antifungal agents, e.g. benzoic acid), vitamins and mixtures thereof.

By "flavour modulator," it is meant here an ingredient capable of enhancing sweetness, to block bitterness, to enhance umami, to reduce sourness or liquorice taste, to enhance saltiness, to enhance a cooling effect, or any combinations of the foregoing. The flavour modulators are also called trigeminal sensates.

In the context of this invention "physical parameter" designates any measurable and/or quantifiable physical property of a fragrance or flavour ingredient. Examples of such physical parameters are mass, density, or number of carbon atoms.

In the context of this invention, the terms "computing system" designate any electronic calculation device, whether unitary or distributed, capable of receiving numerical inputs and providing numerical outputs by and to any sort of interface, digital and/or analog. Typically, a computing system designates either a computer executing a software having access to data storage or a client-server architecture wherein the data and/or calculation is performed at the server side while the client side acts as an interface.

In the context of this invention, the terms "digital identifier" refer to any computerised identifier, such as one used in a computer database, representing a physical object, such as a fragrance or flavour ingredient.

In the context of this invention, the terms "dedicated software" refer to a set of instructions or routines means to be executed by a computing system, said instructions or routines being representative of a digital algorithm.

In the context of this invention, the term "sustainability" refers to any measure of an impact on the environment of a particular ingredient or composition thereof.

FIG. 1 is a representation of a particular embodiment of the method 100 object of the present invention. This computer-implemented fragrance or flavour ingredient or composition of said ingredients physical parameter database construction method 100, comprises:

a step 105 of collection, upon a computer interface, of at least one value representative of a measurable sustainability physical parameter, said physical parameter being representative of an intrinsic sustainability physical parameter of the fragrance or flavour ingredient or of a measurable sustainability physical parameter representative of a manufacturing process associated to the fragrance or flavour ingredient, said fragrance or flavour ingredient being associated to a fragrance or flavour ingredient digital identifier, at least one said physical parameter being representative of:
  the carbon renewability of the fragrance or flavour ingredient,
  the biodegradability of the fragrance or flavour ingredient,
  a quantity or proportion of upcycled ingredients used to obtain the fragrance or flavour ingredient,
  a quantity or proportion of biotechnologically processed ingredients used to obtain the fragrance or flavour ingredient,
  a quantity or proportion of renewable raw materials used to obtain the fragrance or flavour ingredient,
  the carbon dioxide equivalent footprint of the fragrance or flavour ingredient or
  a quantity or proportion of organic raw materials used to obtain the fragrance or flavour ingredient,
a step 110 of computation, by a computing device, of a sustainability impact digital index for the fragrance or flavour ingredient digital identifier and
a step 115 of storing, in a database, the computed sustainability impact digital index for the fragrance or flavour ingredient digital identifier.

It should be noted that the method 100 may correspond to an equivalent step 100 of database construction in any method object of the present invention.

The step 105 of collection may be performed, for example, by a keyboard, mouse and/or touchscreen adapted to interact with a computing system in such a way to collect user input. In variants, the means of collection are logical in nature, such as a network port of a computing system configured to receive an input command transmitted electronically. Such an input means may be associated to a GUI (Graphic User Interface) shown to a user or an API (Application programming interface). In other variants, the means of collection may be a sensor configured to measure a specified physical parameter relevant for the intended use case.

Below are a few examples of adapted means of collection for particular physical parameters:
  a GUI configured to receive user input relative to the value of a number of renewable carbon atoms in a fragrance or flavour ingredient, a value of a total number of renewable carbon atoms in said fragrance or flavour ingredient and/or a value of a ratio of number of renewable carbon atoms over the total number of carbon atoms for said fragrance or flavour ingredient,
  an API configured to connect to a renewable carbon atom mapping database, associating, for a determined fragrance or flavour ingredient digital identifier, a number of renewable carbon atoms, a total number of carbon atoms and/or a value of a ratio of number of renewable carbon atoms over the total number of carbon atoms for said fragrance or flavour ingredient,
  a sensor configured to perform a carbon 14 isotope labelling operation for renewable biomass carbons in an ingredient,
  a sensor configured to determine the presence of a fragrance or flavour ingredient over time in a controlled environment to determine the biodegradability of said fragrance or flavour ingredient or
  a sensor configured to determine a quantity of waste generated to produce a given quantity of a fragrance or flavour ingredient.

The step 110 of computation is performed, for example, by a computing system configured to run a dedicated software. The algorithmic nature of this step depends on the desired output for the targeted sustainability impact digital index.

Some examples are disclosed below:

Relative to the carbon renewability of a fragrance or flavour ingredient, the step 110 of computation may algorithmically compute a ratio of a number of renewable carbon atoms in the fragrance or flavour ingredient divided by the total number of carbon atoms in the fragrance or flavour ingredient. Such carbons may originate from any one of three sources: biomass, upcycled or recycled carbon and be labelled as such in different indicators or aggregated into a single indicator.

Relative to the biodegradability of a fragrance or flavour ingredient, the step 110 of computation may algorithmically compute a statistical value (such as an average or median) corresponding to a remaining quantity or proportion of fragrance or flavour ingredient within a determined assay timeframe. Such a quantity or proportion may be set by a user, to fit to a desired definition of biodegradation (readily, inherently, ultimately, or partially biodegradable). A more biodegradable fragrance or flavour ingredient is closer to 0% remaining initial matter than a less biodegradable fragrance or flavour ingredient.

Such biodegradability may be expressed in terms of "readily biodegradable" or "inherently, ultimately biodegradable" proportion or quantity. Readily biodegradable refers to ingredients measured in OECD 301/310 lab tests, above 60% of biodegradation in less than 28 days, with a 10-day window. Inherently, Ultimately Biodegradable refers to ingredients measured in above 60% at 28 days and above 60% at 60 days in OECD 301/310 lab tests and above 70% at 28 days in OECD 302 lab tests(Includes readily biodegradable).

Relative to the carbon waste performance of a process, also known as carbon economy, to manufacture a fragrance or flavour ingredient, the step 110 of computation may algorithmically compute a ratio of a number of carbon atoms in the fragrance or flavour ingredient divided by the total number of carbon atoms in the reagents/reactants necessary to obtain said fragrance or flavour ingredient. The higher the value of this ratio, the less carbon is wasted during the manufacturing process.

Relative to the number of catalytic steps performance of a process to manufacture a fragrance or flavour ingredient, the step 110 of computation may algorithmically compute a ratio of a number of catalytic steps necessary to obtain the fragrance or flavour ingredient divided by a total number of steps necessary to obtain the fragrance or flavour ingredient. The higher the value of this ratio, the fewer stoichiometric steps/reagents are used in the manufacturing process.

Relative to the hazardousness performance of a process to manufacture a fragrance or flavour ingredient, the step 110 of computation may algorithmically compute a number of risk phrases associated to at least one reactant/reagent necessary to obtain the fragrance or flavour ingredient. A risk phrase is an entry of a hazardous material classification and labelling scheme, such as the one managed by the Globally Harmonized System of Classification and Labelling of Chemicals ("GHS"). More advanced embodiment may associate, to risk phrases, a severity rating based upon the hazard level associated to said risk phrases. As a function of the number of risk phrases and, optionally, the average hazard level of these risk phrases, a value representative of the hazardousness performance may be set.

In other, more advanced embodiments, a decision matrix may be put in place as a function of an F-plot analysis allowing for the definition of the upper limit of the frequency risk phrases, for which the range can be defined using GHS category 3, as it represents the largest proportion. In such embodiments not only is the hazard-level category used, but this category is crossed with a frequency or risk phrases for the evaluated ingredient, allowing for a finer indicator definition. That is, a GHS category 4 ingredient may be, in fact, less hazardous than a GHS category 5 depending on the number of risk phrases associated to said ingredient.

Relative to the quantity of waste generated to obtain the fragrance or flavour ingredient, the step 110 of computation may algorithmically compute the absolute value of global wastes (solid, liquid, gaseous, including wastes dissolved in the water), generated for the production of one kilogram of purified final material. Such a ratio may be obtained by dividing the normalised desired material by the sum of all reactants, starting materials and solvents.

Relative to the quantity or proportion of upcycled ingredients used to obtain the fragrance or flavour ingredient, the step 110 of computation may algorithmically compute a ratio or quantity of raw material leftovers from other manufacturing processes, by-products or waste issued from transformation processes and/or plastic waste upcycled into high-value chemicals divided by the total quantity of ingredients in the formula.

Relative to the quantity or proportion of biotechnologically ingredients used to obtain the fragrance or flavour ingredient, the step 110 of computation may algorithmically compute a ratio or quantity of raw material originating from a biotechnology process (i.e. fermentation, biotransformation, or enzymatic process), including ingredients issued directly from biotechnology and ingredients issued via biotechnology for which an intermediate is produced by a biotech process and then converted further by chemical processes.

Relative to the quantity or proportion of renewable raw materials used to obtain the fragrance or flavour ingredient, the step 110 of computation may algorithmically compute a ratio of a number of renewable reactants/reagents used divided by a total number of reactants/reagents used. A reactant/reagent is said to be renewable if this reactant/reagent is at least 50% carbon renewable.

Relative to the carbon dioxide equivalent footprint necessary to obtain the fragrance or flavour ingredient, the step 110 of computation may algorithmically compute at least one of the following: resource extraction, a distance travelled from extraction sites to the fragrance or flavour ingredient site, a transportation type, or an energy consumption to obtain the fragrance or flavour ingredient for example, an energy source type.

Relative to the quantity of waste generated to obtain the fragrance or flavour ingredient, the step 110 of computation may algorithmically compute a value representative of quantity or proportion of waste generated during the fragrance or flavour ingredient manufacturing process.

Relative to the quantity of water used or wasted to obtain the fragrance or flavour ingredient, the step 110 of computation may algorithmically compute a value representative of quantity or proportion of water used during the fragrance or flavour ingredient manufacturing process. Such a value may be calculated according to the "Aware" methodology.

Other parameters may further be included, such as labour-related parameters (fair wages in the manufacturing process, appropriate working hours, absence of child labour, absence of forced labour, absence of discrimination), health and safety-related parameters (absence of workers' occupational health risks, safety management system for workers) or skill and knowledge-related parameters (skill training among workers).

Relative to labour-related parameters, such parameters may be inspired by WBCSD Social Life Cycle Metrics for Chemical Products (WBCSD, November 2016, ISBN: 978-2-940521-52-4).

Such an index takes into account seven indicators under three social areas, which include all mandatory areas for workers:
  basic rights & needs:
    fair wages,
    appropriate working hours,
    freedom of association, collective bargaining, and
      labour relations,
    no child labour,
    no forced labour, human trafficking, and slavery and
    no discrimination,
  health & safety:
    workers' occupational health risks and
    safety management system for workers,
  skills & knowledge:
    skills, knowledge, and employability.

As a result, an employees & suppliers index may be generated for each supplier and manufacturing site. This score can then reflect into each ingredient. If a ingredient is both manufactured and purchased, a weighted average may be calculated as a function of past manufacture and purchase volumes.

Finally, a weighted average taking into account the quantity of ingredients in the fragrance can be calculated to obtain an employees & social indicator for a fragrance or flavour composition.

In preferred embodiments, the method 100 further comprises a step of normalising (not represented) the computed values for at least one targeted sustainability impact digital index for at least two fragrance or flavour ingredients. This step of normalising can be performed by a computing device configured to run a dedicated software. Algorithmically, this step of normalising can be done, for example, by dividing the fragrance or flavour ingredient samples into quintiles, ranked from best ("A") to worst ("E"). Obviously, any other normalisation techniques, such as between a range of 0 to 100 for example, can be used.

In the context of an indicator representative of waste generation, the normalisation process may be based upon an existing referential, such as the ones disclosed in R. A. Sheldon; Green Chem. 2007, (9), pp 1273-1283.

The step 115 of storing is performed, for example, by a computing system configured to run a dedicated software. During this step 115 of storing, a database, either unitary or distributed, is accessed and entries are either created, deleted, or modified. Each fragrance or flavour ingredient digital identifier is associated with a value for at least one sustainability impact digital index computed.

Comprehensive storing of sustainability impact digital indexes allows for greater modelling of the environmental impact of fragrance or flavour ingredients used by perfumers.

Figure 7:
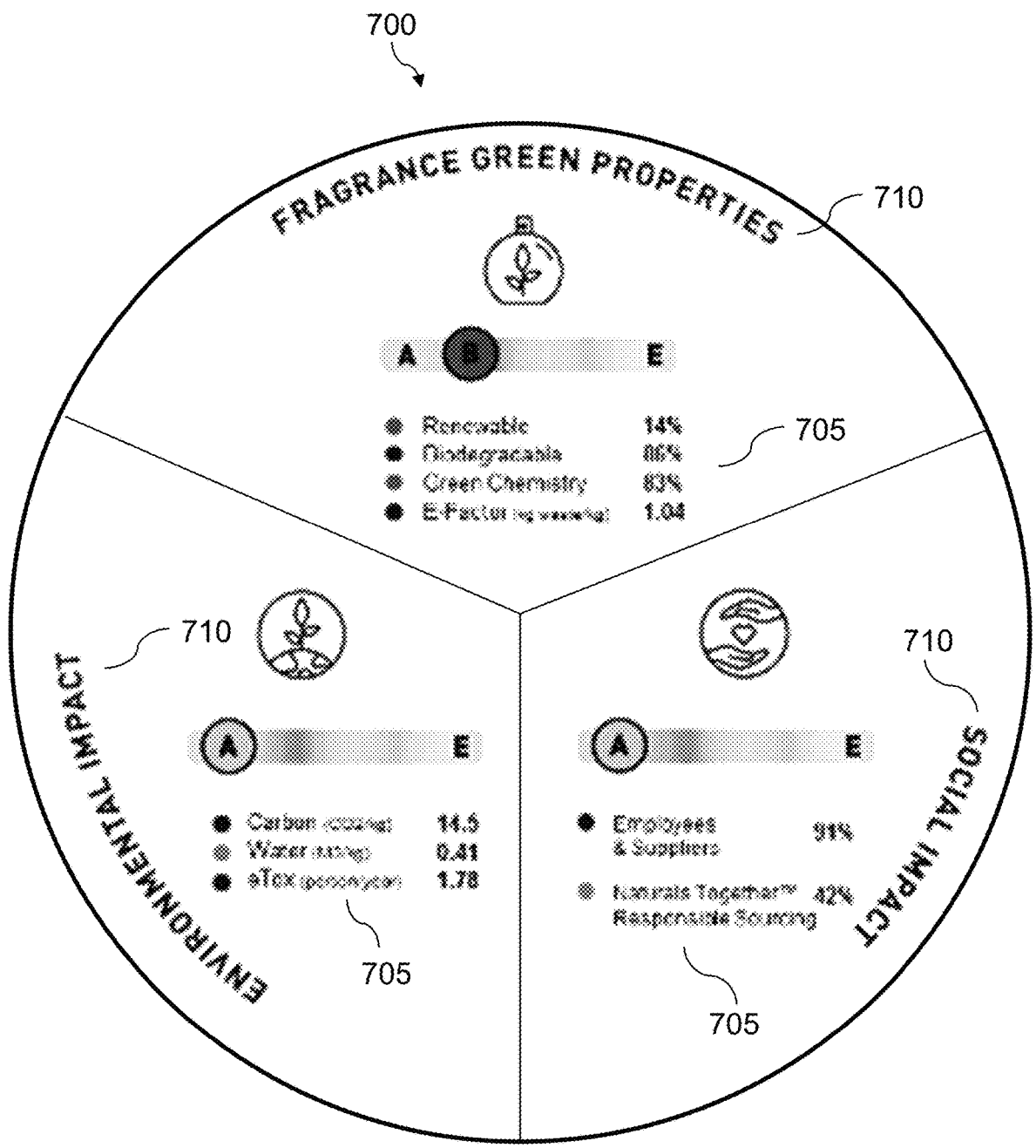
FIG. 7 represents, schematically, a graphical representation of a scorecard representing values for sustainability performance digital indexes for a given fragrance or flavour ingredient.

The values stored in the database may be shown in an intuitive manner to users, such as perfumers. Such a representation is shown in FIG. 7, in which the scores for independent indexes 705 are shown divided into categories 710, each category representing an aggregate score, corresponding to an aggregate sustainability impact digital indicator.

In particular embodiments, at least one sustainability impact digital index is representative of:
- a ratio of a number of carbons of the fragrance or flavour ingredient over a number of carbons in the reactants and reagents used to obtain the fragrance or flavour ingredient,
- a number of catalytic steps required to obtain the fragrance or flavour ingredient,
- a hazardousness of the reactants, solvents and reagents used to obtain the fragrance or flavour ingredient,
- a quantity or proportion of essential oils used to obtain the fragrance or flavour ingredient,
- a surface area of land used to obtain the fragrance or flavour ingredient,
- a quantity of waste generated to obtain the fragrance or flavour ingredient,
- a quantity or proportion of water used to obtain the fragrance or flavour ingredient,
- a quantity or proportion of palm oil or palm oil derivatives used to obtain the fragrance or flavour ingredient and/or
- the environmental toxicity of the fragrance or flavour ingredient.

Such embodiments are disclosed above, in terms of data processing, and require the appropriate data collection.

For natural ingredients green chemistry, such indicators may be altered so that:
- atom economy is replaced by extraction yield of pure material and
- catalysis efficiency is replaced by extraction energy consumption to obtain a determined quantity of final ingredient or a to process a determined quantity of pure material.

The indicator representative of hazardousness may be adapted to the specific extraction processes of green chemistry.

Further physical parameters may be, for example, a quantity or proportion of certified sourcing of the fragrance or flavour ingredient.

Further physical parameters may be, for example, a quantity or proportion of particular allergens of the fragrance or flavour ingredient.

Further physical parameters may be, for example, an absence of legally banned ingredients in the fragrance or flavour ingredient.

In particular embodiments, the method 100 further comprises a step 120 of determination, by a computing device, of an aggregate sustainability impact digital indicator as a function of at least two different sustainability impact digital indexes for the fragrance or flavour ingredient digital identifier.

The step 120 of determination is performed, for example, by a computing system configured to run a dedicated software. The algorithmic nature of this step depends on the desired output for the targeted aggregate sustainability impact digital indicator.

In a particular embodiment, a weighted average of sustainability impact digital indexes, such as those shown in FIG. 7, may be used.

Figure 2:
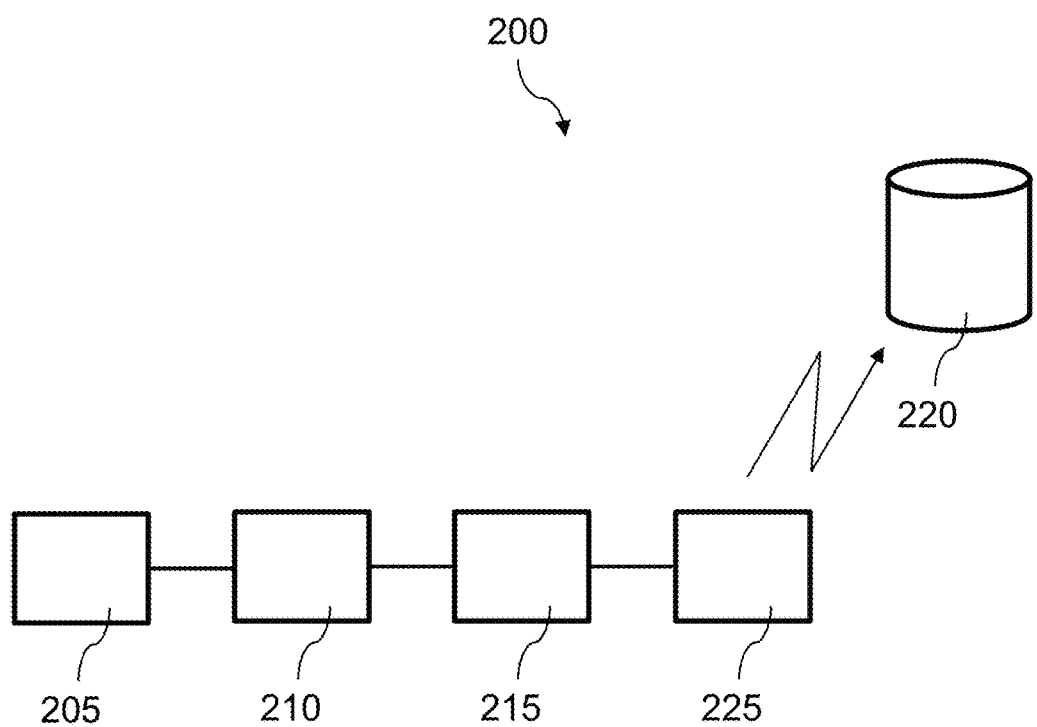
FIG. 2 represents, schematically, a particular embodiment of a system capable of implementing the database construction method, which is the object of the present invention.

FIG. 2 is a representation of a particular embodiment of the device 200 object of the present invention. This fragrance or flavour ingredient or composition of said ingredients physical parameter database construction device 200 comprises:

- a means 205 of collection, upon a computer interface, of at least one value representative of a measurable sustainability physical parameter, said physical parameter being representative of an intrinsic sustainability physical parameter of the fragrance or flavour ingredient or of a measurable sustainability physical parameter representative of a manufacturing process associated to the fragrance or flavour ingredient, said fragrance or flavour ingredient being associated to a fragrance or flavour ingredient digital identifier, at least one said physical parameter being representative of:
  - the carbon renewability of the fragrance or flavour ingredient,
  - the biodegradability of the fragrance or flavour ingredient,
  - a quantity or proportion of upcycled ingredients used to obtain the fragrance or flavour ingredient,
  - a quantity or proportion of biotechnologically processed ingredients used to obtain the fragrance or flavour ingredient,
  - a quantity or proportion of renewable raw materials used to obtain the fragrance or flavour ingredient,
  - the carbon dioxide equivalent footprint of the fragrance or flavour ingredient or
  - a quantity or proportion of organic raw materials used to obtain the fragrance or flavour ingredient,
- a means 210 of computation, by a computing device, of a sustainability impact digital index for the fragrance or flavour ingredient digital identifier and
- a means 215 of storing, in a database 220, the computed sustainability impact digital index for the fragrance or flavour ingredient digital identifier.

Particular implementation details of the above means have been disclosed in regard to corresponding steps, such as those disclosed in the description of FIG. 1. As it is understood, the means 205 of collection may be either physical (sensor, input system) or logical (API or GUI). The means 210 of computation and the means 215 of storing may be a software element ran by a computing system in charge of executing an algorithm corresponding to the corresponding step.

The database 220 may be hosted locally or remotely. Such a database 220 corresponds to any digital registry or memory, such as a hard drive or random-access memory.

Figure 3:
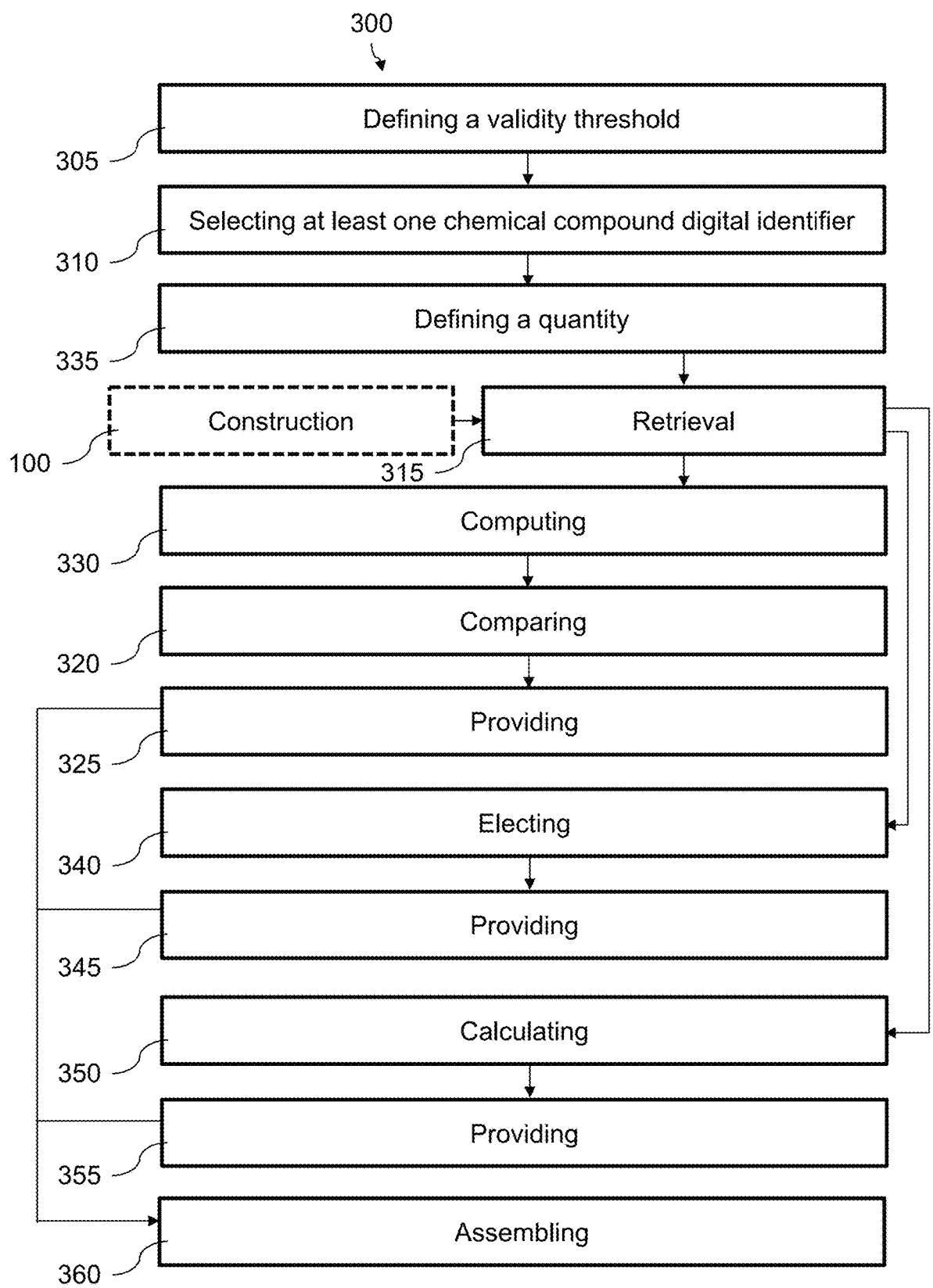
FIG. 3 represents, schematically and in the form of a flowchart, a particular succession of steps of a first embodiment of the fragrance or flavour composition method, which is the object of the present invention.

FIG. 3 is a representation of a particular embodiment of the method 300 object of the present invention. This computer-implemented fragrance or flavour composition method 300 comprises:

- a step 305 of defining, upon a computer interface, a value representative of a sustainability impact digital index or of an aggregate sustainability impact digital indicator validity threshold for at least one fragrance or flavour ingredient in the fragrance or flavour composition, said fragrance or flavour ingredient being associated to a fragrance or flavour ingredient digital identifier, or to the fragrance or flavour composition, at least one said physical parameter being representative of:
  - the carbon renewability of the fragrance or flavour ingredient,
  - the biodegradability of the fragrance or flavour ingredient,
  - a quantity or proportion of upcycled ingredients used to obtain the fragrance or flavour ingredient,
  - a quantity or proportion of biotechnologically processed ingredients used to obtain the fragrance or flavour ingredient, a quantity or proportion of renewable raw materials used to obtain the fragrance or flavour ingredient, the carbon dioxide equivalent footprint of the fragrance or flavour ingredient or a quantity or proportion of organic raw materials used to obtain the fragrance or flavour ingredient, a step 310 of selecting, upon a computer interface, at least one fragrance or flavour ingredient digital identifier, a step 315 of retrieval, by a computing device, from a fragrance or flavour ingredient physical parameter database obtained, for example, according to the method disclosed in regard to FIG. 1, of a sustainability impact digital index or of an aggregate sustainability impact digital indicator as a function of at least one said fragrance or flavour ingredient digital identifier, a step 320 of comparing, by a computing device, as a function of at least one selected fragrance or flavour ingredient digital identifier, a sustainability impact digital index or of an aggregate sustainability impact digital indicator retrieved to the validity threshold defined and a step 325 of providing, upon a computer interface, an indicator representative of the result of the step of comparing.

The step 305 of defining may be performed, for example, by a keyboard, mouse and/or touchscreen adapted to interact with a computing system in such a way to collect user input. In variants, the means of collection are logical in nature, such as a network port of a computing system configured to receive an input command transmitted electronically. Such an input means may be associated to a GUI (Graphic User Interface) shown to a user or an API (Application programming interface).

In a particular variant, during the step 305 of defining, a user is presented with a GUI comprising a digital component in charge of collecting user input, via keyboard input to collect a numerical value corresponding to the desired validity threshold.

Figure 5:
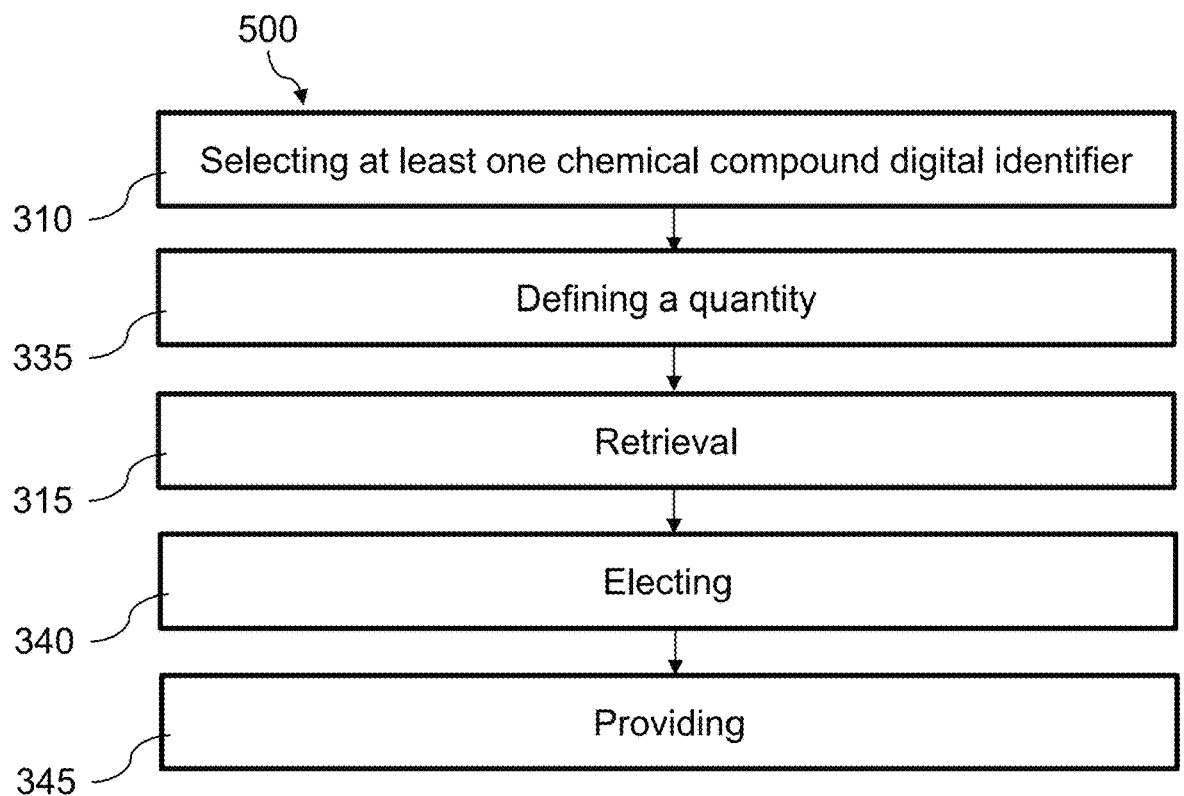
FIG. 5 represents, schematically and in the form of a flowchart, a particular succession of steps of a second embodiment of the fragrance or flavour composition method, which is the object of the present invention.
Figure 6:
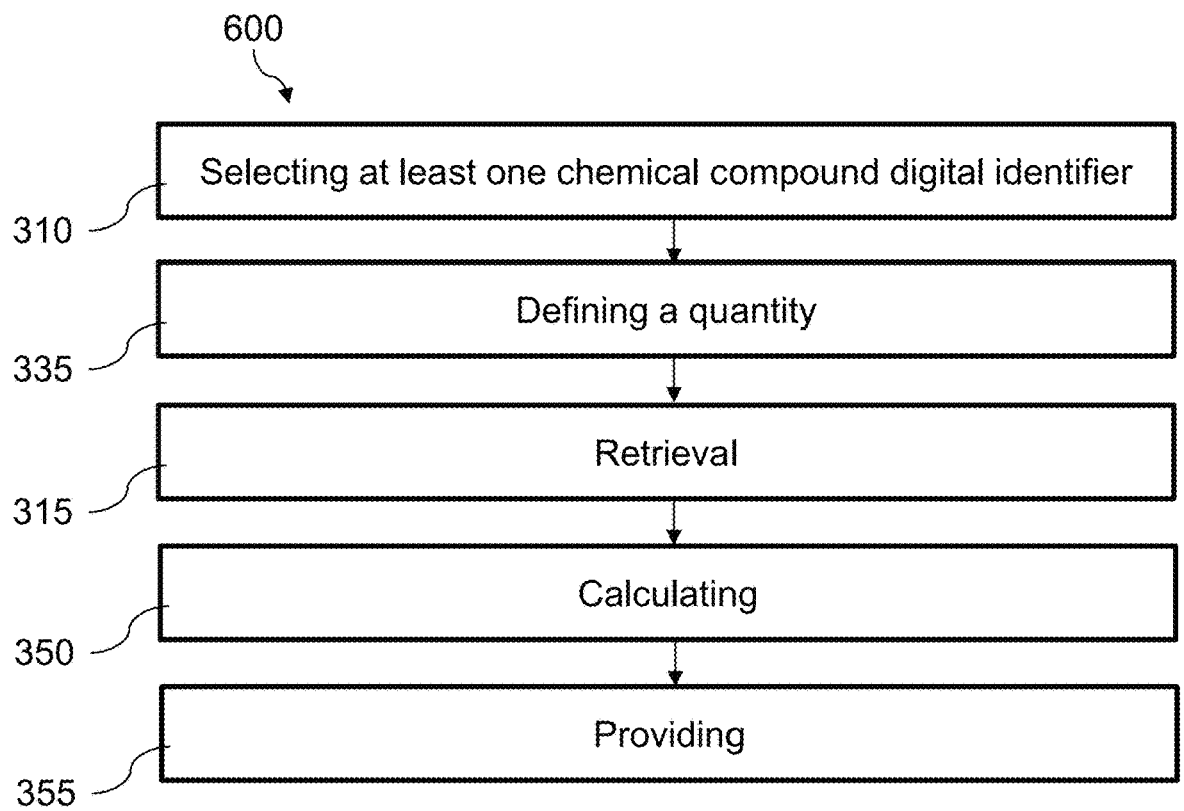
FIG. 6 represents, schematically and in the form of a flowchart, a particular succession of steps of a third embodiment of the fragrance or flavour composition method, which is the object of the present invention.
Figure 8:
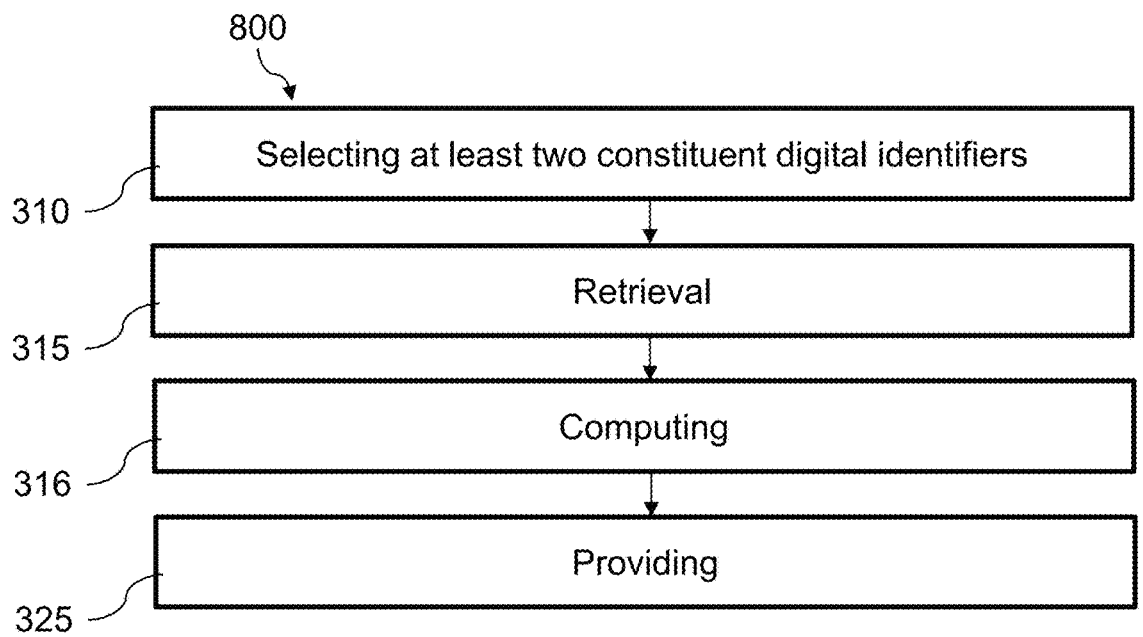
FIG. 8 represents, schematically and in the form of a flowchart, a particular succession of steps of a fourth embodiment of the fragrance or flavour composition method, which is the object of the present invention
Figure 9:
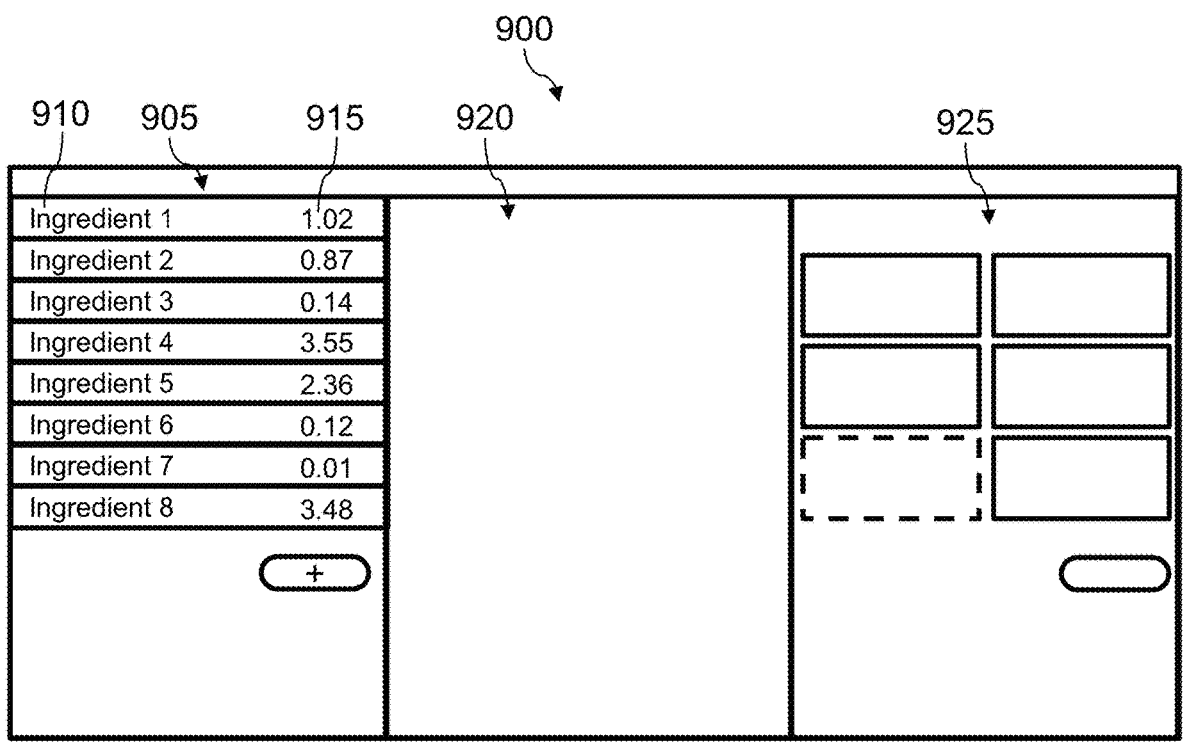
FIG. 9 represents, schematically, a graphical representation of a graphic user interface implementing the methods object of the present invention.

Such a variant is presented in FIG. 9, which shows a displayed computer interface 900, comprising:

a section 905 dedicated to ingredient selection and configuration within a fragrance or flavour composition, showing in this instance a composition of eight ingredients 910, each associated to a quantity 915, a section 920 dedicated to displaying the performance of each selected ingredient with regards to at least one indicator or index such as disclosed above and a section 925 dedicated to smart fragrance or flavour composition, showing formulation improvement capabilities (in the forms of buttons for example, the selected capability being shown as with a dashed line outline) that can be triggered by a user, such as:

threshold-based improvements, such as disclosed in regard to FIG. 3, ingredient replacement, such as disclosed in regard to FIG. 5, ingredient removal, such as disclosed in regard to FIG. 3, ingredient quantity adjustment, such as disclosed in regard to FIG. 6 and/or global composition scoring, such as disclosed in regard to FIG. 8.

It should be noted that a global validity threshold can be replaced, or complemented, by secondary validity thresholds corresponding, for example, to a specific sustainability impact digital index or aggregate sustainability impact digital indicator.

The step 310 of selecting can be performed analogously to the step 305 of defining.

In a particular variant, during the step 310 of selecting, a user is presented with a GUI comprising a digital component in charge of collecting user input via mouse selection of alphanumeric labels corresponding to fragrance or flavour ingredient digital identifiers.

In particular embodiments, during the step 310 of selecting, a quantity corresponding to a particular fragrance or flavour ingredient digital identifier may be defined by a user.

The step 315 of retrieval is performed, for example, by a computing system configured to run a dedicated software. During this step 315, a fragrance or flavour ingredient digital identifier may be sent to a server accessing a database to select at least one sustainability impact digital index or of an aggregate sustainability impact digital indicator as a function associated to said fragrance or flavour ingredient digital identifier.

The step 320 of comparing is performed, for example, by a computing system configured to run a dedicated software. During this step 320 of comparing, at least one sustainability impact digital index or of an aggregate sustainability impact digital indicator retrieved is compared to the corresponding validity threshold defined during the step 305 of defining.

The step 325 of providing is performed, for example, by a computing system configured to run a dedicated software. During this step 325 of providing, the result of the step 320 of comparison may be shown upon a GUI or transmitted electronically via an API to another system.

In a particular variant, a GUI shows the compatibility of a composition set by a user, by selecting at least one fragrance or flavour ingredient digital identifier, with a defined validity threshold.

In particular embodiments, such as shown in FIG. 3, the method 300 further comprises, downstream of the step of 315 retrieval, a step 330 of computing, by a computing device, an aggregate sustainability impact digital indicator as a function of at least one sustainability impact digital index retrieved, said aggregate sustainability impact digital indicator being used in the step 320 of comparing.

The step 330 of computing may be performed analogously to the step 120 of determination disclosed in regard to FIG. 1.

Corresponding validity thresholds may be defined, during the step 305 of defining, by a user or another digital system.

In particular embodiments, such as shown in FIG. 3, the method 300 further comprises a step 335 of defining, upon a computer interface, a value representative of a quantity of fragrance or flavour ingredient, said value being used in the step of computing.

This step 335 of defining a quantity may be performed analogously to the step 310 of selecting a fragrance or flavour ingredient digital identifier.

The value representative of a quantity may either be a proportion (in ppm for example), a number of moles or a weight measured in milligrams. The relative quantities between the different fragrance or flavour ingredients selected allow for the definition of a composition sustainability impact digital index or of a composition aggregate sustainability impact digital indicator by way of weighted average. Without defining such quantities, a standard average, a minimum function (the lowest score applies) or a maximum function (the highest score applies) may be used.

In particular embodiments, such as shown in FIG. 3, the method 300 further comprises:

a step 340 of electing, by a computing device, at least one candidate fragrance or flavour ingredient digital identifier as a replacement for at least one selected fragrance or flavour ingredient digital identifier as a function of said at least one selected fragrance or flavour ingredient digital identifier and a step 345 of providing, upon a computer interface, at least one candidate fragrance or flavour ingredient digital identifier elected.

The step 340 of electing is performed, for example, by a computing system configured to run a dedicated software. In an example of a corresponding algorithm, at least one other fragrance or flavour ingredient digital identifier is screened and at least one sustainability impact digital index or aggregate sustainability impact digital indicator value for said fragrance or flavour ingredient digital identifier is computed. The impact of said sustainability impact digital index or aggregate sustainability impact digital indicator value upon the composition may be then calculated. If that impact is positive (i.e., the score of the composition improves), that candidate fragrance or flavour ingredient digital identifier may be presented upon a computer interface for possible selection by either a user or another digital system.

In more advanced embodiments, at least one fragrance or flavour ingredient digital identifier is associated to olfactive properties values, such as tonality, volatility, capacity to be perceived after a certain time, capacity to be perceived at a certain distance and so on. The candidate fragrance or flavour ingredient digital identifier selected for screening, in those embodiments, are selected for their proximity to the values of the fragrance or flavour ingredient digital identifier selected for replacement.

In other embodiments, a combination of fragrance or flavour ingredient digital identifiers may be screened as candidates to replace a single selected fragrance or flavour ingredient digital identifier.

In other embodiments, a single fragrance or flavour ingredient digital identifiers may be screened as candidates to replace a plurality of selected fragrance or flavour ingredient digital identifiers.

Such a step 340 of election may employ a variety of election rules, which may vary according to the particular implementation of the method 300 object of the present invention. Such rules may be, for example:

the candidate ingredient has the same CAS (for "Chemical Abstracts Society" of the American Chemical Society) number than an ingredient in the composition, meaning that at least one constitutive chemical compound of an ingredient (potentially multi-compound) is shared between the candidate ingredient and the original ingredient to be replaced, the candidate ingredient has a percentage of renewable carbon that is at least equal to the percentage of renewable carbon of the original ingredient to be replaced, the existence of a price for a factory/creation center for which the composition is materialized and/or the naturally sourced percentage, as per ISO9235/IFRA (for "International Fragrance Association") definition, for the candidate ingredient that is different to the naturally sourced IFRA of the original ingredient to be replaced.

The step 345 of providing may be performed analogously to the step 325 of providing described above.

In particular embodiments, such as shown in FIG. 3, the method 300 further comprises:

a step 350 of calculating, by a computing device, a value representative of a quantity or proportion of at least one selected fragrance or flavour ingredient digital identifier as a function of the validity threshold defined and a step 355 of providing, upon a computer interface, the quantity calculated.

The step 350 of calculating is performed, for example, by a computing system configured to run a dedicated software. In an example of a corresponding algorithm, at least one quantity of a selected fragrance or flavour ingredient digital identifier is adjusted to meet the validity threshold defined. This typically implies a system of equations to be solved as other fragrance or flavour ingredient digital identifiers may be part of the composition and present their own impact on the validity threshold defined. Such a change in quantity, or proportion, may be either an increase or decrease in quantity to meet the defined validity threshold for a sustainability impact digital index or aggregate sustainability impact digital indicator.

In more advanced embodiments, at least one fragrance or flavour ingredient digital identifier is associated to olfactive properties values, such as tonality, volatility, capacity to be perceived after a certain time, capacity to be perceived at a certain distance and so on. The replacement quantity or proportion for a fragrance or flavour ingredient digital identifier, in those embodiments, is calculated to minimise the impact on the olfactive properties values of the targeted fragrance or flavour ingredient digital identifier.

In other embodiments, a combination of quantities or proportions for fragrance or flavour ingredient digital identifiers may be provided to improve the performance of the composition.

The step 355 of providing may be performed analogously to the step 325 of providing described above.

In particular embodiments, such as shown in FIG. 3, the method 300 further comprises a step 360 of assembling the fragrance or flavour composition as a function of at least one selected fragrance or flavour ingredient digital identifier.

The step 360 of assembling is performed, for example, by any combination of means, devices and systems used to assemble a composition and known by persons skilled in the art.

Figure 4:
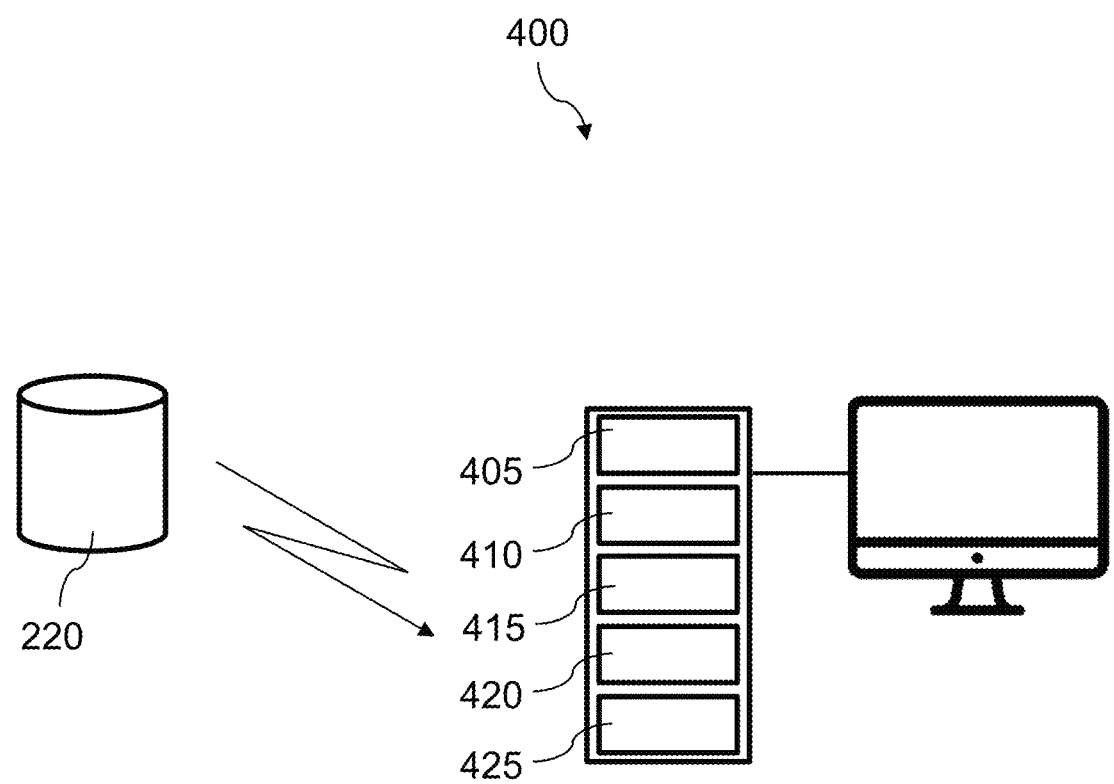
FIG. 4 represents, schematically, a particular embodiment of a system capable of implementing the fragrance or flavour composition method, which is the object of the present invention.

FIG. 4 is a representation of a particular embodiment of the device 200 object of the present invention. This fragrance or flavour composition device 400 comprises:

a means 405 of defining, upon a computer interface, a value representative of a sustainability impact digital index or of an aggregate sustainability impact digital indicator validity threshold for at least one fragrance or flavour ingredient in the fragrance or flavour composition, said fragrance or flavour ingredient being associated to a fragrance or flavour ingredient digital identifier, or to the fragrance or flavour composition, at least one said physical parameter being representative of:

the carbon renewability of the fragrance or flavour ingredient, the biodegradability of the fragrance or flavour ingredient, a quantity or proportion of upcycled ingredients used to obtain the fragrance or flavour ingredient, a quantity or proportion of biotechnologically processed ingredients used to obtain the fragrance or flavour ingredient, a quantity or proportion of renewable raw materials used to obtain the fragrance or flavour ingredient, the carbon dioxide equivalent footprint of the fragrance or flavour ingredient or a quantity or proportion of organic raw materials used to obtain the fragrance or flavour ingredient, a means 410 of selecting, upon a computer interface, at least one fragrance or flavour ingredient digital identifier, a means 415 of retrieval, by a computing device, from a fragrance or flavour ingredient physical parameter database 220 obtained, for example, according to the method disclosed in regard to FIG. 1, of a sustainability impact digital index or of an aggregate sustainability impact digital indicator as a function of at least one said fragrance or flavour ingredient digital identifier a means 420 of comparing, by a computing device, as a function of at least one selected fragrance or flavour ingredient digital identifier, a sustainability impact digital index or of an aggregate sustainability impact digital indicator retrieved to the validity threshold defined and a means 425 of providing, upon a computer interface, an indicator representative of the result of the step of comparing.

Particular implementation details of the above means have been disclosed in regard to corresponding steps, such as those disclosed in the description of FIG. 2.

FIG. 5 is a representation of a particular embodiment of the method 500 object of the present invention. This computer-implemented fragrance or flavour composition method 500 comprises:

a step 310 of selecting, upon a computer interface, at least one fragrance or flavour ingredient digital identifier, a step 315 of retrieval, by a computing device, from a fragrance or flavour ingredient physical parameter database obtained, for example, according to the method disclosed in regard to FIG. 1, of a sustainability impact digital index or of an aggregate sustainability impact digital indicator as a function of at least one said fragrance or flavour ingredient digital identifier, at least one said physical parameter being representative of:

the carbon renewability of the fragrance or flavour ingredient, the biodegradability of the fragrance or flavour ingredient, a quantity or proportion of upcycled ingredients used to obtain the fragrance or flavour ingredient, a quantity or proportion of biotechnologically processed ingredients used to obtain the fragrance or flavour ingredient, a quantity or proportion of renewable raw materials used to obtain the fragrance or flavour ingredient, the carbon dioxide equivalent footprint of the fragrance or flavour ingredient or a quantity or proportion of organic raw materials used to obtain the fragrance or flavour ingredient, a step 340 of electing, by a computing device, at least one candidate fragrance or flavour ingredient digital identifier as a replacement for at least one selected fragrance or flavour ingredient digital identifier as a function of said at least one selected fragrance or flavour ingredient digital identifier and a step 345 of providing, upon a computer interface, at least one candidate fragrance or flavour ingredient digital identifier elected.

This method 500 corresponds to an alternative method to the method 300 disclosed in regard to FIG. 3 in that no validity threshold is defined. Rather, this method 500 focuses on providing candidate fragrance or flavour ingredient digital identifiers as a replacement for selected fragrance or flavour ingredient digital identifiers.

Particular implementation examples for the constitutive steps of this method 500 are described in regard to FIG. 3.

FIG. 6 is a representation of a particular embodiment of the method 500 object of the present invention. This computer-implemented fragrance or flavour composition method 600, comprises:

a step 310 of selecting, upon a computer interface, at least one fragrance or flavour ingredient digital identifier, a step 315 of retrieval, by a computing device, from a fragrance or flavour ingredient physical parameter database obtained, for example, according to the method disclosed in regard to FIG. 1, of a sustainability impact digital index or of an aggregate sustainability impact digital indicator as a function of at least one said fragrance or flavour ingredient digital identifier, at least one said physical parameter being representative of:

the carbon renewability of the fragrance or flavour ingredient, the biodegradability of the fragrance or flavour ingredient, a quantity or proportion of upcycled ingredients used to obtain the fragrance or flavour ingredient, a quantity or proportion of biotechnologically processed ingredients used to obtain the fragrance or flavour ingredient, a quantity or proportion of renewable raw materials used to obtain the fragrance or flavour ingredient, the carbon dioxide equivalent footprint of the fragrance or flavour ingredient or a quantity or proportion of organic raw materials used to obtain the fragrance or flavour ingredient, a step 350 of calculating, by a computing device, a value representative of a quantity or proportion of at least one selected fragrance or flavour ingredient digital identifier as a function of the validity threshold defined and a step 355 of providing, upon a computer interface, the quantity calculated.

This method 600 corresponds to an alternative method to the method 300 disclosed in regard to FIG. 3 in that no validity threshold is defined. Rather, this method 600 focuses on providing alternative quantities or proportions for selected fragrance or flavour ingredient digital identifiers as a replacement for initially selected fragrance or flavour ingredient digital identifier quantities or proportions.

FIG. 8 is a representation of a particular embodiment of the method 500 object of the present invention. This computer-implemented fragrance or flavour composition method 800 comprises:

a step 310 of selecting, upon a computer interface, at least two fragrance or flavour ingredient digital identifiers, a step 315 of retrieval, by a computing device, from a fragrance or flavour ingredient physical parameter database obtained, for example, according to the method of FIG. 1, of a sustainability impact digital index or of an aggregate sustainability impact digital indicator as a function of at least two said fragrance or flavour ingredient digital identifier, at least one said physical parameter being representative of:

the carbon renewability of the fragrance or flavour ingredient, the biodegradability of the fragrance or flavour ingredient, a quantity or proportion of upcycled ingredients used to obtain the fragrance or flavour ingredient, a quantity or proportion of biotechnologically processed ingredients used to obtain the fragrance or flavour ingredient, a quantity or proportion of renewable raw materials used to obtain the fragrance or flavour ingredient,
the carbon dioxide equivalent footprint of the fragrance or flavour ingredient or
a quantity or proportion of organic raw materials used to obtain the fragrance or flavour ingredient,
a step 316 of computing an aggregate sustainability impact digital indicator as a function of at least two sustainability impact digital index retrieved and
a step 325 of providing, upon a computer interface, the computed aggregate sustainability impact digital indicator.

This method 800 corresponds to an alternative method to the method 300 disclosed in regard to FIG. 3 in that no validity threshold is defined. Rather, this method 800 focuses on providing composition-level performance indicator and/or index by aggregation of individual ingredient indicator and/or index. Such an aggregation, performed during the step 316 of computing, may correspond to an average or weighted average of individual ingredient indicators and/or indexes.

In such a method 800, another aspect of being able to indicate an average value, together with a coverage value to indicate how much data was used for the calculation. The coverage gives information on data completeness, thus as a result data reliability.

In particular embodiments, any method object of the present invention may further comprise a step (not represented) of determination of key ingredients both fitting an intended olfactive profile (or tonality) of the composition and providing highly favorable sustainability physical parameter values. For example, if a particular composition is intended to smell like lavender, if one of the constitutive ingredients contributes to the smell of lavender (tonality of the ingredient) presents above-average values for the measured sustainability physical parameters, this ingredient may be determined as key for the composition. Such ingredient may be highlighted upon a GUI, for example.

The invention claimed is:

1. A computer-implemented method for assembling sustainable fragrance or flavour composition, the method comprising:
    a step of defining, upon a computer interface, a value representative of a sustainability impact digital index or of an aggregate sustainability impact digital indicator validity threshold for at least one fragrance or flavour ingredient in a fragrance or flavour composition, said fragrance or flavour ingredient being associated to a fragrance or flavour ingredient digital identifier, or to a fragrance or flavour composition digital identifier, at least one physical parameter being representative of at least one of:
        the carbon renewability of the fragrance or flavour ingredient,
        the biodegradability of the fragrance or flavour ingredient,
        a quantity or proportion of upcycled ingredients used to obtain the fragrance or flavour ingredient,
        a quantity or proportion of biotechnologically processed ingredients used to obtain the fragrance or flavour ingredient,
        a quantity or proportion of renewable raw materials used to obtain the fragrance or flavour ingredient or
        a quantity or proportion of organic raw materials used to obtain the fragrance or flavour ingredient,
    a step of selecting, upon a computer interface, at least one fragrance or flavour ingredient digital identifier,
    retrieving, from a fragrance or flavour ingredient physical parameter database, a sustainability impact digital index or an aggregate sustainability impact digital indicator as a function of at least one said fragrance or flavour ingredient digital identifier,
    a step of comparing, by a computing device, as a function of at least one selected fragrance or flavour ingredient digital identifier, a sustainability impact digital index or of an aggregate sustainability impact digital indicator retrieved to the validity threshold defined
    a step of providing, upon a computer interface, an indicator representative of the result of the step of comparing
    a step of calculating, by a computing device, a value representative of a quantity or proportion of at least one selected fragrance or flavour ingredient digital identifier as a function of the validity threshold defined,
    a step of providing, upon a computer interface, the quantity calculated and
    a step of assembling the fragrance or flavour composition as a function of at least one selected fragrance or flavour ingredient digital identifier and the quantity calculated.

2. The method according to claim 1, which further comprises, downstream of the step of retrieval, a step of computing, by a computing device, an aggregate sustainability impact digital indicator as a function of at least one sustainability impact digital index retrieved, said aggregate sustainability impact digital indicator being used in the step (320) of comparing.

3. The method according to claim 2, which further comprises a step of defining, upon a computer interface, a value representative of a quantity of fragrance or flavour ingredient, said value being used in the step of computing.

4. The method according to claim 1, which further comprises:
    a step of electing, by a computing device, at least one candidate fragrance or flavour ingredient digital identifier as a replacement for at least one selected fragrance or flavour ingredient digital identifier as a function of said at least one selected fragrance or flavour ingredient digital identifier and
    a step of providing, upon a computer interface, at least one candidate fragrance or flavour ingredient digital identifier elected.

5. The method according to claim 1 wherein said physical parameter database is constructed by a construction method, comprising:
    a step of collection, upon a computer interface, of at least one value representative of a measurable sustainability physical parameter, said physical parameter being representative of an intrinsic sustainability physical parameter of the fragrance or flavour ingredient or of a measurable sustainability physical parameter representative of a manufacturing process associated to the fragrance or flavour ingredient, said fragrance or flavour ingredient being associated to a fragrance or flavour ingredient digital identifier, at least one physical parameter being representative of at least one of:
        the carbon renewability of the fragrance or flavour ingredient,
        the biodegradability of the fragrance or flavour ingredient,
        a quantity or proportion of upcycled ingredients used to obtain the fragrance or flavour ingredient, a quantity or proportion of biotechnologically processed ingredients used to obtain the fragrance or flavour ingredient,
a quantity or proportion of renewable raw materials used to obtain the fragrance or flavour ingredient,
the carbon dioxide equivalent footprint of the fragrance or flavour ingredient or
a quantity or proportion of organic raw materials used to obtain the fragrance or flavour ingredient,
a step of computation, by a computing device, of a sustainability impact digital index for the fragrance or flavour ingredient digital identifier and
a step of storing, in a database, the computed sustainability impact digital index for the fragrance or flavour ingredient digital identifier.

6. The method according to claim 5, in which at least one sustainability impact digital index is representative of:
a ratio of a number of carbons of the fragrance or flavour ingredient over a number of carbons in the reactants and reagents used to obtain the fragrance or flavour ingredient,
a number of catalytic steps required to obtain the fragrance or flavour ingredient,
a hazardousness of the reactants, solvents and reagents used to obtain the fragrance or flavour ingredient,
a quantity or proportion of essential oils used to obtain the fragrance or flavour ingredient,
a surface area of land used to obtain the fragrance or flavour ingredient,
a quantity of waste generated to obtain the fragrance or flavour ingredient,
a quantity or proportion of water used to obtain the fragrance or flavour ingredient,
a quantity or proportion of palm oil or palm oil derivatives used to obtain the fragrance or flavour ingredient and/or
the environmental toxicity of the fragrance or flavour ingredient.

7. The method according to claim 6, in which at least one sustainability impact digital index is representative of a number of catalytic steps required to obtain the fragrance or flavour ingredient.

8. The method according to claim 5, in which at least one sustainability impact digital index is representative of a hazardousness of the reactants, solvents and reagents used to obtain the fragrance or flavour ingredient.

9. The method according to claim 5, in which at least one sustainability impact digital index is representative of a ratio of a number of carbons of the fragrance or flavour ingredient over a number of carbons in the reactants and reagents used to obtain the fragrance or flavour ingredient.

10. The method according to claim 5, which further comprises a step of determination, by a computing device, of an aggregate sustainability impact digital indicator as a function of at least two different sustainability impact digital indexes for the fragrance or flavour ingredient digital identifier.

11. A computer-implemented method for assembling sustainable fragrance or flavour composition, the method comprising:
a step of selecting, upon a computer interface, at least one fragrance or flavour ingredient digital identifier,
a step of retrieval, by a computing device, from a fragrance or flavour ingredient physical parameter database of a sustainability impact digital index or of an aggregate sustainability impact digital indicator as a function of at least one said fragrance or flavour ingredient digital identifier, at least one physical parameter being representative of at least one of:
the carbon renewability of the fragrance or flavour ingredient,
the biodegradability of the fragrance or flavour ingredient,
a quantity or proportion of upcycled ingredients used to obtain the fragrance or flavour ingredient,
a quantity or proportion of biotechnologically processed ingredients used to obtain the fragrance or flavour ingredient,
a quantity or proportion of renewable raw materials used to obtain the fragrance or flavour ingredient,
the carbon dioxide equivalent footprint of the fragrance or flavour ingredient or
a quantity or proportion of organic raw materials used to obtain the fragrance or flavour ingredient,
a step of electing, by a computing device, at least one candidate fragrance or flavour ingredient digital identifier as a replacement for the selected at least one fragrance or flavour ingredient digital identifier as a function of a sustainability impact digital index or of an aggregate sustainability impact digital indicator of said at least one selected and one elected fragrance or flavour ingredient digital identifier and
a step of providing, upon a computer interface, at least one candidate fragrance or flavour ingredient digital identifier elected,
a step of calculating, by a computing device, a value representative of a quantity or proportion of at least one elected fragrance or flavour ingredient digital identifier,
a step of providing, upon a computer interface, the quantity calculated and
a step of assembling the fragrance or flavour composition as a function of at least one elected fragrance or flavour ingredient digital identifier.

12. A computer-implemented method for assembling sustainable fragrance or flavour composition, the method comprising:
a step of selecting, upon a computer interface, at least one fragrance or flavour ingredient digital identifier,
a step of retrieval, by a computing device, from a fragrance or flavour ingredient physical parameter database of a sustainability impact digital index or of an aggregate sustainability impact digital indicator as a function of at least one said fragrance or flavour ingredient digital identifier, at least one physical parameter being representative of at least one of:
the carbon renewability of the fragrance or flavour ingredient,
the biodegradability of the fragrance or flavour ingredient,
a quantity or proportion of upcycled ingredients used to obtain the fragrance or flavour ingredient,
a quantity or proportion of biotechnologically processed ingredients used to obtain the fragrance or flavour ingredient,
a quantity or proportion of renewable raw materials used to obtain the fragrance or flavour ingredient,
the carbon dioxide equivalent footprint of the fragrance or flavour ingredient or
a quantity or proportion of organic raw materials used to obtain the fragrance or flavour ingredient,
a step of calculating, by a computing device, a value representative of a quantity or proportion of at least one selected fragrance or flavour ingredient digital identifier as a function of a validity threshold defined and a step of providing, upon a computer interface, the quantity calculated, and a step of assembling the fragrance or flavour composition as a function of the quantity calculated of at least one selected fragrance or flavour ingredient digital identifier.

13. A computer-implemented method for assembling sustainable fragrance or flavour composition, the method comprising:

a step of selecting, upon a computer interface, at least two fragrance or flavour ingredient digital identifiers, a step of retrieval, by a computing device, from a fragrance or flavour ingredient physical parameter database of a sustainability impact digital index, for each ingredient digital identifier or an aggregate sustainability impact digital indicator as a function of at least two said fragrance or flavour ingredient digital identifier, at least one physical parameter being representative of at least one of:

the carbon renewability of the fragrance or flavour ingredient, the biodegradability of the fragrance or flavour ingredient, a quantity or proportion of upcycled ingredients used to obtain the fragrance or flavour ingredient, a quantity or proportion of biotechnologically processed ingredients used to obtain the fragrance or flavour ingredient, a quantity or proportion of renewable raw materials used to obtain the fragrance or flavour ingredient, the carbon dioxide equivalent footprint of the fragrance or flavour ingredient or a quantity or proportion of organic raw materials used to obtain the fragrance or flavour ingredient, a step of computing an aggregate sustainability impact digital indicator as a function of at least two sustainability impact digital index retrieved a step of providing, upon a computer interface, the computed aggregate sustainability impact digital indicator, and a step of assembling the fragrance or flavour composition as a function of at least one selected fragrance or flavour ingredient digital identifier.

* * * * *